(12) United States Patent
Hawkins

(10) Patent No.: US 7,172,071 B2
(45) Date of Patent: Feb. 6, 2007

(54) METHOD AND APPARATUS FOR USE OF A VACUUM PACKAGE FOR ALLOGRAFT MATERIAL

(75) Inventor: H. Gene Hawkins, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 343 days.

(21) Appl. No.: 10/634,468

(22) Filed: Aug. 5, 2003

(65) Prior Publication Data
US 2005/0029150 A1  Feb. 10, 2005

(51) Int. Cl.
*A61B 17/06* (2006.01)
(52) U.S. Cl. .................................. 206/438; 206/366
(58) Field of Classification Search ............... 206/438, 206/363, 364, 365, 366, 221, 216, 219; 366/130, 366/182.1, 182.3, 139
See application file for complete search history.

(56) References Cited

U.S. PATENT DOCUMENTS

| | | | |
|---|---|---|---|
| 3,770,026 A | 11/1973 | Isenberg | |
| 4,046,145 A | 9/1977 | Choksi et al. | |
| 4,060,082 A | 11/1977 | Lindberg et al. | |
| 4,073,321 A | 2/1978 | Moskowitz | |
| 4,551,135 A | 11/1985 | Gorman et al. | |
| 4,743,229 A | 5/1988 | Chu | |
| 4,820,306 A | 4/1989 | Gorman et al. | |
| 5,425,580 A | 6/1995 | Beller | |
| 5,601,077 A | 2/1997 | Imbert | |
| 5,811,061 A | 9/1998 | Martinson et al. | |
| 5,908,054 A | 6/1999 | Safabash et al. | |
| 5,910,315 A | 6/1999 | Stevenson et al. | |
| 5,951,160 A | 9/1999 | Ronk | |
| 5,957,166 A | 9/1999 | Safabash | |
| 6,049,026 A | 4/2000 | Muschler | |
| 6,234,190 B1 | 5/2001 | Fischer et al. | |
| 6,286,670 B1 | 9/2001 | Smith | |
| 6,406,175 B1 | 6/2002 | Marino | |
| 6,648,133 B1 | 11/2003 | Smith et al. | |
| 2001/0016703 A1 | 8/2001 | Wironen et al. | |
| 2001/0037091 A1 | 11/2001 | Wironen et al. | |

FOREIGN PATENT DOCUMENTS

| | | |
|---|---|---|
| WO | WO01/08630 | 2/2001 |
| WO | WO02/39946 | 5/2002 |

OTHER PUBLICATIONS

Betz, "Limitations of Autograft and Allograft: New Synthetic Solutions", Orthopedics, May 2002, vol. 25, No. 5/Supplement, pp. 561-570.
California Transplant Services, Inc., "Human Freeze-dried Tissue", 1994, 1 page.
Partial European Search Report for EP 04 25 4705.

*Primary Examiner*—Shian T. Luong
(74) *Attorney, Agent, or Firm*—Harness, Dickey & Pierce, P.L.C.

(57) ABSTRACT

A method and apparatus for packaging, reconstituting, and delivering an allograft material formed from a first container, and a second container. The first container is operable for containing and maintaining the allograft material at a vacuum. The first container is further operable for providing a favorable negative pressure during reconstitution of the allograft. The first container is also operable for use as an allograft delivery device to a surgical site.

16 Claims, 4 Drawing Sheets

METHOD AND APPARATUS FOR USE OF A VACUUM PACKAGE FOR ALLOGRAFT MATERIAL

FIELD OF THE INVENTION

The present invention is generally related to an allograft packaging apparatus and packaging and delivery methods, and more particularly to a method and apparatus for packaging and reconstituting allograft using a vacuum system to assist the reconstitution.

BACKGROUND OF THE INVENTION

The natural joints and bones of the body often undergo degenerative changes due to a variety of etiologies. When these degenerative changes become advanced and irreversible, it may ultimately become necessary to replace or repair a damaged bone or joint. When such a procedure becomes necessary, the bone may be repaired with an implant secured with allograft material such as de-mineralized bone material or bone chips. Other uses of allograft material include repairing or mending bone fractures or shattered bones that may occur from extreme trauma. Allograft may also be used to fill bone screw holes made during an orthopedic medical procedure or chips in teeth.

When a surgical procedure requires the use of bone particles as a filler material or to promote bone growth, the surgeon may recycle bone particles from the patient (autograft), or use donor bone particles (allograft). Allograft is frequently used due to the lack of quality or quantity of autograft. Bone particles may be freeze dried and stored for later use. Typically, it is desirable to store these freeze dried particles under a negative pressure in order to prolong their shelf-life. In order to implant allograft that has been freeze dried into a surgical site, the allograft must be reconstituted using a liquid such as patient blood, platelet concentrate, or saline. Platelet concentrate (from the patient, centrifuged during surgery) and patient blood are desirable to prevent the bone from rejecting the graft and can be harvested during surgery.

Typical methods for reconstituting allograft involve soaking the allograft in a liquid. This method relies primarily on the capillary action of the liquid in the pores of the allograft. Blood has been found to exhibit poor capillary action when compared to thinner liquids, such as saline or water. This deficiency in capillarity may result in a prepared allograft that has not been thoroughly wetted. Thus, prior art methods require time to adequately wet the capillaries, or pores, of allograft particles. While allograft can be reconstituted prior to use, the need for more allograft than expected may prolong a surgical procedure.

What is needed is an improved apparatus and packaging system to more expediously reconstitute allograft with various liquids and deliver the reconstituted allograft to a surgical site, while ensuring a thorough wetting of allograft particles.

SUMMARY OF THE INVENTION

In accordance with the teaching of the present invention, a method and apparatus for packaging and delivering allograft is disclosed. In one form, the present invention provides a packaging system for allograft wherein the allograft is contained at a vacuum within a chamber defined by a first container having a first and second sealing devices. The first container is positioned within a second container that is also pulled to a vacuum. In another form, an allograft material is positioned within a first container having a first and second openings. The first opening is sealed with a sealing device while the second opening is covered with a gas permeable membrane. The first container is inserted into a second container such that the gas permeable membrane defines an interface between the first and second containers. A seal between the first and second containers allows the allograft material to be maintained at a negative pressure.

In yet another form, the present invention provides a method of reconstituting allograft under a negative pressure wherein a reconstituting liquid is injected into an allograft container that is separated from a second container by a gas permeable membrane.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiments of a method and apparatus for packaging, reconstituting, and delivering an allograft are merely exemplary in nature and is in no way intended to limit the invention, its application, or uses. Moreover, while the present invention is described in detail with reference to an allograft material, it will be appreciated by those skilled in the art that the present invention is not limited to an allograft material, but may also be used with any other material that requires reconstitution or wetting and could benefit from reconstitution under a vacuum. It should also be appreciated that the reconstituting liquid may be platelet concentrate, blood, aspirate, or other liquids capable of reconstituting the allograft material.

Figure 1:
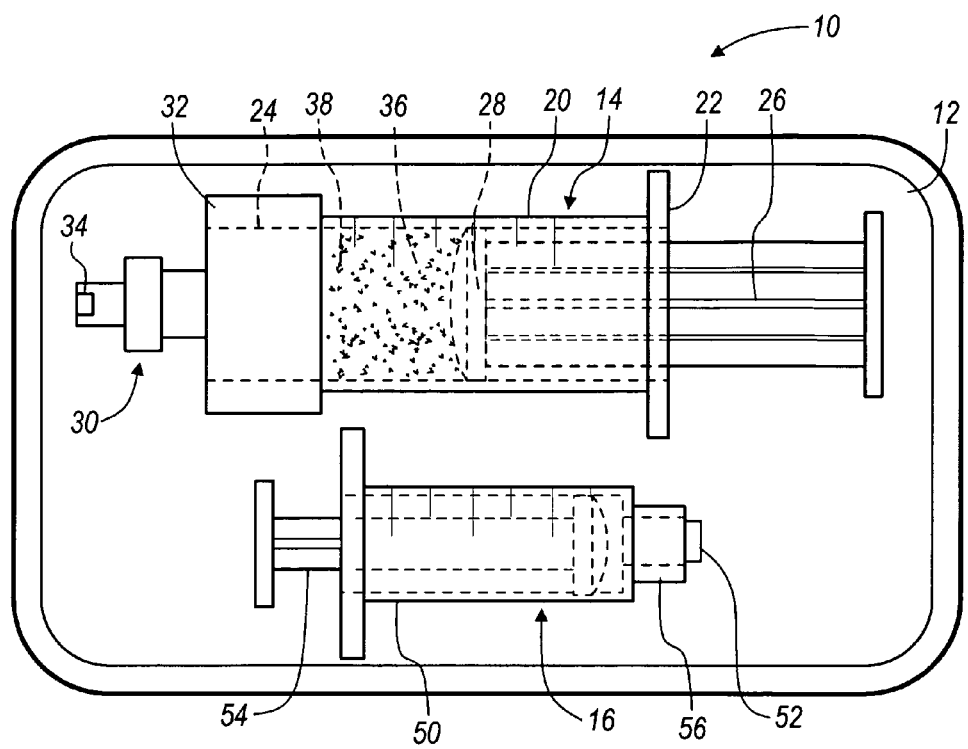
FIG. 1 illustrates an allograft packaging system or kit of the present invention.

FIG. 1 illustrates an allograft packaging system 10 wherein an outer container 12 encloses a first container 14 and a second container 16, such as a syringe. Outer container 12 is preferably configured to maintain first container 14 and second container 16 in a sterile environment under a negative pressure and, as an example, may be a flexible vacuum bag. In this regard, the first container 14 and second container 16 are placed in outer container 12 and a vacuum is drawn in the outer container 12.

First container 14 includes a barrel 20 having a proximal end 22, an outlet end 24, a plunger 26, a plunger seal 28, and a valve 30. Valve 30 includes a female leur fitting 32 adapted to couple in fluid communication with barrel 20, and a leur fitting 34 adapted to couple with second container 16. Valve 30 is removeably coupled to outlet end 24 of barrel 20 with leur fitting 32. Optionally, valve 30 is a one-way vented valve that is operable to respond to a differential pressure and allow fluids to flow out of first container 14, and may be selectively opened. Collectively, barrel 20, plunger seal 28, and valve 30 define a chamber 36. Chamber 36 may be prepackaged with an allograft 38. The allograft 38 includes bone chips or de-mineralized bone material (DBM) that has been freeze dried for preservation, although chamber 36 could also be packed with other porous, bone substitute materials, autograft, synthetic materials such as ceramics, or combinations thereof. The chamber 36 is pulled to a vacuum before first container 14 is positioned in outer container 12. Plunger 26 is fitted with a removeable clip 44 that interferes with proximal end 22 to prevent movement of plunger 26 toward outlet end 24. While first container 14 may be a conventional syringe, first container 14 can also be a Maxxim Medical Part No. 193221 syringe with dosage control that includes an integral member to limit travel of plunger 26, thus eliminating the need for clip 44 can be any other appropriate container. In this manner, allograft 38 can be stored in an environment that is favorable for long or short term preservation. Second container or second container 16 includes a barrel 50 having an outlet end 52, a plunger 54, and a leur fitting 56 positioned at outlet end 52. Second container 16 can be a conventional syringe such as VWR Scientific Part No. BD309604 or any appropriate syringe or container generally having a barrel, a plunger, and a connector.

In manufacture, all components of allograft packaging system 10 are maintained in a sterile environment. First container 14, with plunger 26 inserted therein, is filled with a predetermined amount of allograft 38. Valve 30, in an open position, is removably coupled to barrel 20. Clip 44 is attached to plunger 26, and a vacuum is drawn on allograft 38 within chamber 36 via valve 30. Valve 30 is then closed and removed from the vacuum source. First container 14 and the second container 16 are positioned in outer container 12, and outer container 12 is sealed with a negative pressure therein. The negative pressure within outer chamber 12 is comparable to the negative pressure within chamber 36. Thus provided, the negative pressure within outer chamber 12 can reduce differential pressure stresses on plunger 26, plunger seal 28, valve 30, and clip 44. In this manner, allograft 38 can be provided at a negative pressure within first container 14 that is packaged within an outer container that protects the seals of first container 14.

It would be appreciated that first container 14 may be evacuated by connecting a vacuum source to leur fitting 34 and that multiple first containers 14 may be evacuated simultaneously with the use of a manifold attachment to the vacuum source. It would also be appreciated that valve 30 may be a vent valve and that a plurality of first containers 14 can be evacuated in a vacuum chamber with the vent valve(s) in the vent position. When the vacuum chamber is opened, the vacuum within chamber(s) 36 will be maintained by the integral vent of the vent valve.

When fully assembled, first container 14 and second container 16 are sealed in outer container 12 such that the allograft packaging system 10 provides a sterile, convenient means to provide an allograft implantation system at a surgical site as discussed below.

Figure 2:
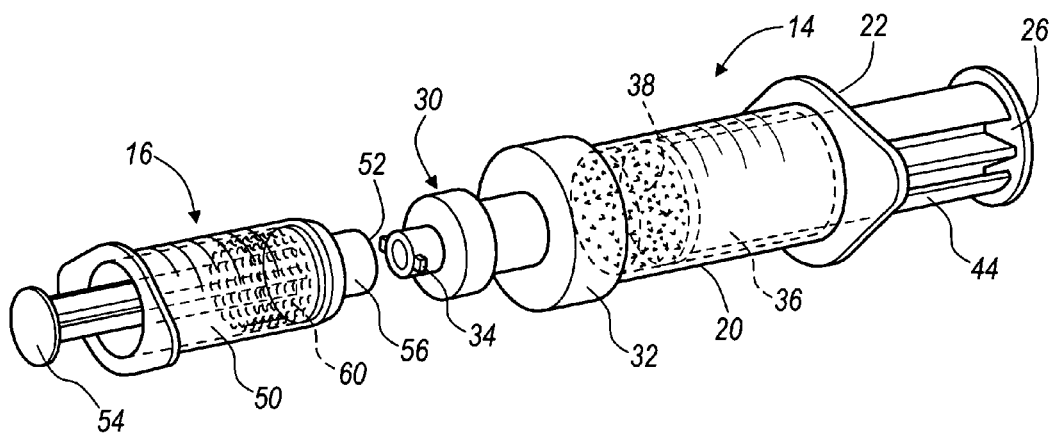
FIG. 2 illustrates an assembled apparatus as provided in the allograft packaging system of FIG. 1.

Referring now to FIG. 2, in preparing allograft 38 for delivery, outer container 12 is opened and first container 14 and a second container 16 are dumped into a sterile field. Second container 16 is used to collect a reconstituting liquid 60 such as platelet concentrate, patient blood, saline, or bone marrow aspirate etc. Leur fitting 56 of second container 16 is connected to leur fitting 34 of valve 30. Valve 30 is opened by turning leur fitting 34 relative to leur fitting 32 and the reconstituting liquid 60 is introduced into first container 14. It would be appreciated that plunger 54 of second container 16 may be depressed in order to inject the reconstituting liquid 60 into first container 14, or that the vacuum within first container 14 may draw the reconstituting liquid 60 from second container 16 into first container 14. In this manner, the vacuum within the pores of allograft 38 draws the reconstituting liquid 60 directly therein regardless of the orientation of second container 16 to first container 14.

It would be appreciated that the use of a vacuum to draw the reconstituting liquid 60 into the voids or pores of allograft 38 will aid the natural capillary action. When the reconstituting liquid 60 has fully wetted the allograft 38, leur fitting 32 can be removed from barrel 20, thus exposing chamber 36 to atmospheric pressure. It would be appreciated that any residual vacuum in chamber 36 would serve to drive more reconstituting liquid 60 into the pores of allograft 38 as the pressure in chamber 26 rises to atmospheric pressure.

Prior to allograft deposition into a surgical site, clip 44 is removed from plunger 26 to allow plunger 26 to force allograft 38 into the surgical site. Thus provided, allograft packaging system 10 allows an allograft 38 to be reconstituted and delivered within the same container thereby minimizing contamination and waste that is associated with a multi-container allograft delivery system.

Figure 3:
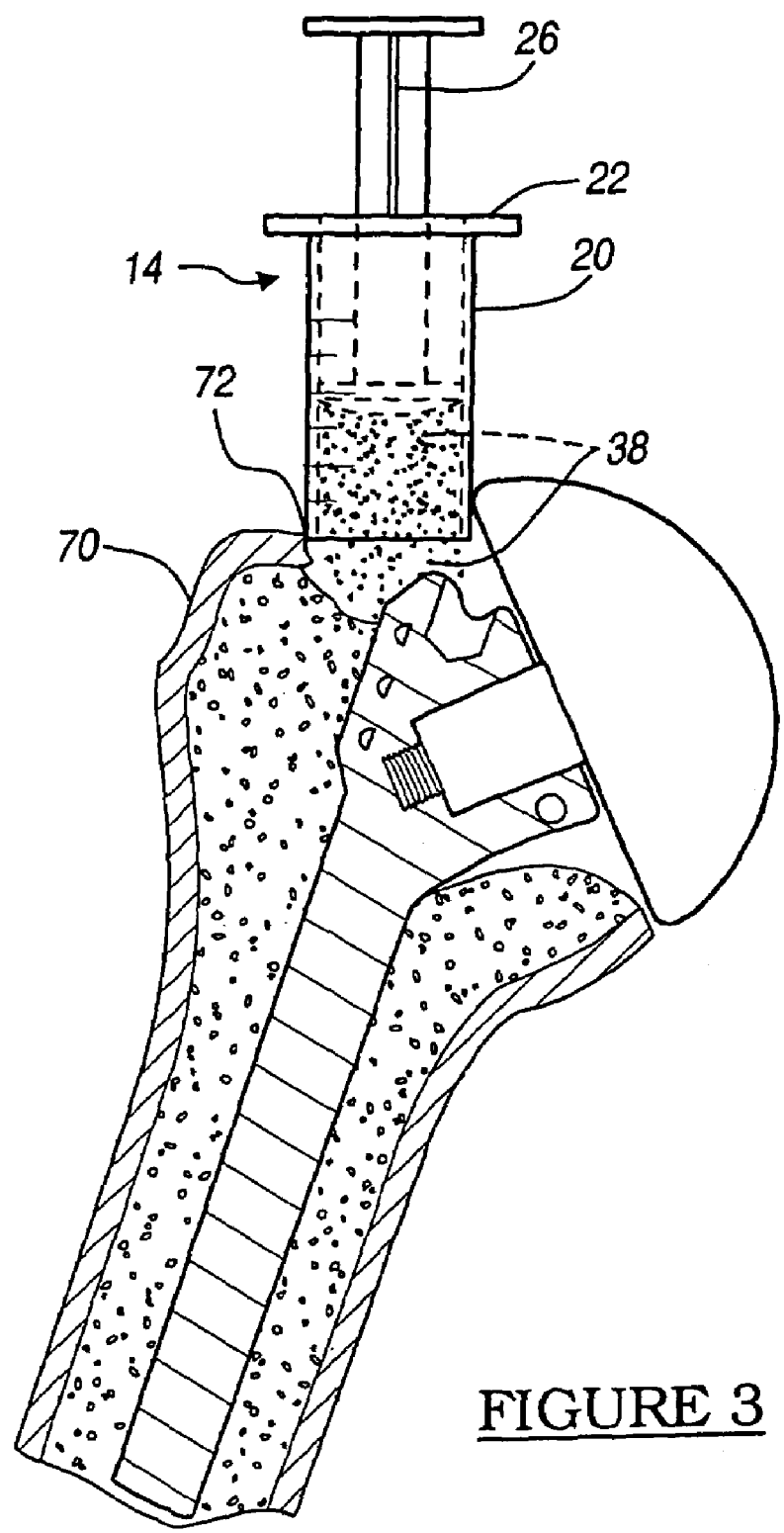
FIG. 3 illustrates the delivery of allograft using a container shown in FIG. 1.

FIG. 3 illustrates a bone 70 with apertures 72. Apertures 72 may be voids in bone 70 resulting from a trauma or a surgical procedure, such as temporary support screw holes or an area of recision for an implant. Outlet end 24 of first container 14, with leur fitting 32 removed, is placed adjacent bone 70 such that allograft 38 can be deposited into aperture 72. A surgeon can depress plunger 96 in order to deliver allograft 38 into aperture 72. It would be appreciated that while FIG. 3 illustrates the delivery of allograft 38 into an aperture 72 with leur fitting 32 removed from first container 14, a reducer or similar device, if desired, may be attached to outlet end 24 to direct allograft into a narrow or remote aperture 72.

Figure 4:
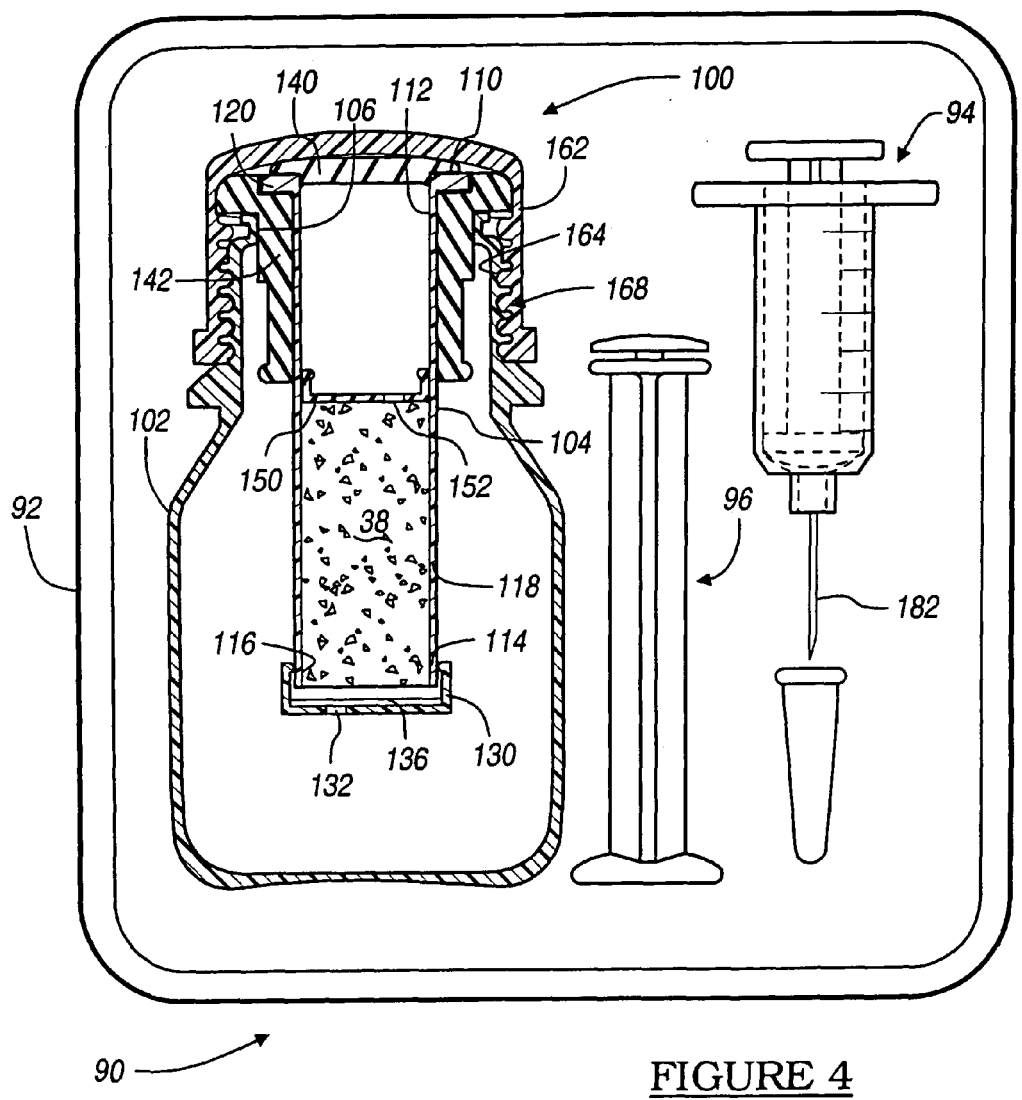
FIG. 4 is another embodiment of the allograft packaging system according to the teachings of the present invention.

FIGS. 4 illustrates an alternate embodiment of allograft packaging system 90 including a sterile tray 92, a third container 94, a plunger 96, and an allograft reconstituting apparatus 100. In the embodiment shown, an exterior portion of allograft reconstituting apparatus 100 is defined by an outer container 102. Outer container 102 encloses a delivery container 104. The outer container 102 defines an opening 106. In the embodiment shown, outer container 102 is a glass bottle, although outer container 102 could be constructed of an equivalent material, such as stainless steel. Additionally, delivery container 104 is shown to be a syringe barrel, although it is anticipated that delivery container 104 could be other suitable containers.

Delivery container 104 has a proximal end 110 defining a plunger opening 112, a delivery end 114 defining a delivery opening 116, a barrel 118 and finger flange 120. A membrane cap 130 is removeably attached to delivery end 114 of delivery container 104 covering delivery opening 116. Membrane cap 130 defines at least one aperture 132. A membrane 136 is interposed between membrane cap 130 and delivery end 114 such that membrane 136 covers aperture 132. Membrane 136 may be constructed of Goretex™, available from W. L. Gore and Associates, Newark, Delaware to provide a seal that passes air or vents and inhibits fluid from passing.

Proximal end 110 has a sealing member 140 attached thereto that is adapted to maintain a negative pressure within delivery container 104. Delivery container 104 has an outer seal 142, adjacent proximal end 110. Outer seal 142 is adapted to seal delivery container 104 with opening 106 of outer container 102. Although outer seal 142 is preferably a modified bottle stopper, it would be appreciated that outer seal 142 could also be a flexible overmolded portion of delivery container 104 that is configured to sealingly engage opening 106. The delivery container 104 has a plunger seal 150 located therein. Plunger seal 150 has at least one seal aperture 152 located therein.

Figure 5:
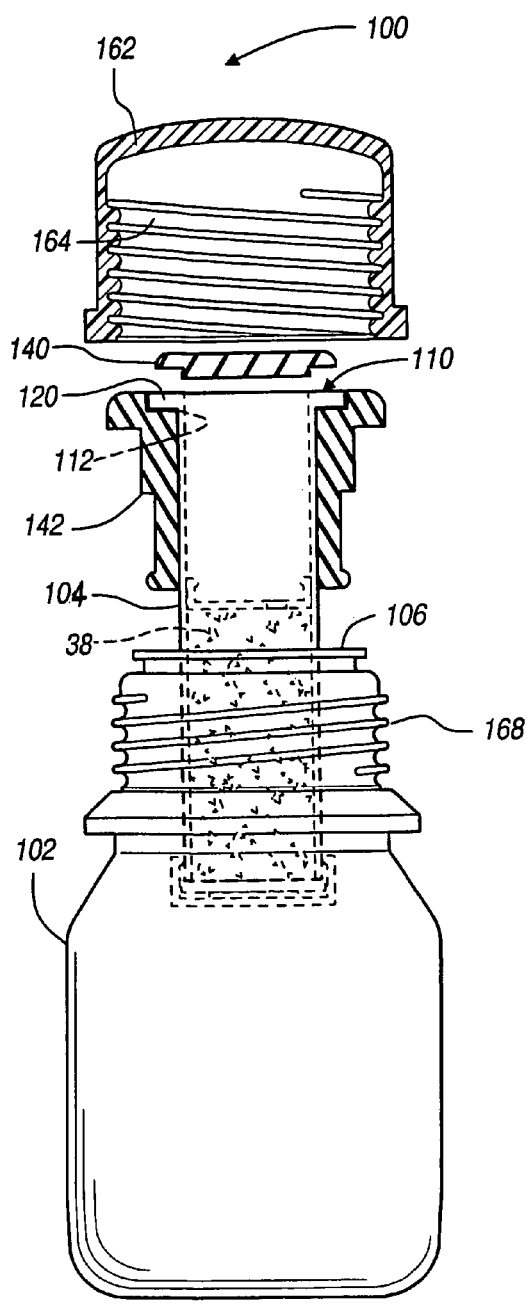
FIG. 5 illustrates the allograft packaging system of FIG. 3 in an exploded view.

Allograft packaging system 90 is shown in FIGS. 4 and 5 to further include plunger 96 that is adapted for insertion within plunger opening 112 of delivery container 104. Allograft packaging system 90 also includes a screw cap 162 within internal threads 164 formed therein. Screw cap 162 is adapted to cover opening 106. The outer container 102 includes external threads 168 formed adjacent opening 106 that are configured to mate with internal threads 164 of the screw cap 162.

During assembly of the allograft reconstituting apparatus 100, outer seal 142 is positioned in delivery container 104 such that outer seal 142 and finger flange 120 are in contact. Membrane 136 is inserted in membrane cap 130 and membrane cap 130 is removeably affixed to delivery container 104. Allograft 38 is loaded into delivery container 104 and plunger seal 150 is inserted into delivery container 104. Sealing member 140 is removeably attached to delivery container 104 and delivery container 104 is partially inserted into outer container 102 just until outer seal 142 contacts outer container 102.

This intermediate apparatus is then placed into a vacuum chamber under a moveable press. The vacuum chamber is evacuated to a desired negative pressure and the moveable press is actuated such that delivery container 104 and outer seal 142 are fully inserted into outer container 102. When the intermediate apparatus is removed from the vacuum chamber, screw cap 162 is threaded onto outer container 102 to produce allograft reconstituting apparatus 100. Allograft reconstituting apparatus 100 is then packaged with a plunger 96 and third container 94 in a sterile tray 92 to form an allograft packaging system 90 as shown in FIG. 4. In the embodiment shown, third container 94 is a syringe, although it would be appreciated that third container 94 can be any container suitable to deliver a reconstituting liquid 60.

Figure 6:
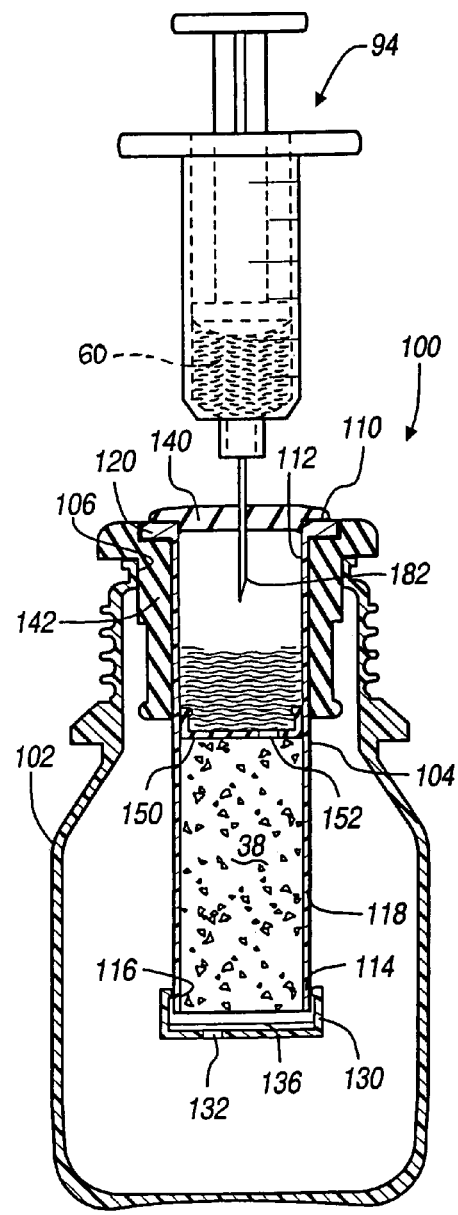
FIG. 6 illustrates a step in reconstituting the allograft contained within the allograft packaging system of FIG. 4.

In preparing allograft 38 for delivery, screw cap 162 is removed from outer container 102. As seen in FIG. 6, a reconstituting liquid 60 is loaded into a third container 94 having a hypodermic needle 182 attached thereto. The hypodermic needle 182 is used to pierce sealing member 140 and the reconstituting liquid 60 is injected into delivery container 104. The liquid 60 is pulled into delivery container 104 due to the vacuum contained therein and is drawn through seal aperture 152 of plunger seal 150. As the liquid 60 is injected into delivery container 104, a localized pressure increase is experienced. The vacuum contained in the outer container 102 and the interstitial voids of allograft 38 draws the liquid 60 through allograft 38 and into the pores of allograft 38. Membrane 136 inhibits the liquid 60 from passing through delivery container 104. In this manner, a negative pressure and associated lack of air molecules is utilized to introduce the liquid 60 into allograft 38 to prepare allograft 38 for implantation. While FIG. 6 illustrates hypodermic needle 182 piercing sealing member 140 for delivery of reconstituting liquid 60 to delivery container 104, it would be appreciated that any coupling means between third container 94 and delivery container 104 that accomplishes the delivery of liquid 60, such as a leur fitting, could also be used.

In contrast, methods of reconstituting allograft that are performed at a constant pressure rely on capillary action for a liquid 60 to enter the allograft pores. While the height of liquid 60 within the allograft does provide some pressure differential across the allograft particles, air molecules within the allograft pores resist the introduction of liquids. This resistance is overcome by the capillarity of the liquid. It should also be noted that while prior art methods require time for the reconstitution of porous materials, or require that a liquid be (washed) several passes through a porous material, the method of the present invention is capable of essentially an instantaneous reconstitution.

As best seen in FIG. 6, a pre-determined amount of liquid 60 is injected into delivery container 104 until allograft 38 is sufficiently reconstituted. Sealing member 140 is then removed from allograft packaging system 90. Upon removal of sealing member 140, the internal pressure of delivery container 104 returns to atmospheric. Plunger 96 is inserted into delivery container 104, and delivery container 104 is then removed from outer container 102. Membrane cap 130 and membrane 136 are removed from delivery container 104 and allograft 38 is delivered to a surgical site by fully inserting plunger 96 into delivery container 104. It would be appreciated that allograft 38 should be surrounded by the liquid 60 prior to allowing the pressure within delivery container 104 to rise to atmospheric in order to take full advantage of the negative pressure within allograft 38.

When using an allograft 38 consisting of bone chips and a platelet concentrate as the reconstituting liquid 60, exemplary results are achieved when using an allograft packaging system 90 that is pulled to between about 28–29 inches of water vacuum and supplied with about 5 cc of bone chips. A physician injects about 3 cc of platelet concentrate into delivery container 104 and then pauses to ensure that the platelet concentrate percolates toward the membrane cap 130. An additional 3 cc of platelet concentrate is injected, and sealing member 140 is removed. It would be appreciated that while this method is successful for larger allograft particle sizes, any dry, particulate material, including powdered allograft, can be reconstituted with this method. When performing the method with small particulate or powdered allograft, or bone cement, exemplary results are achieved when liquids are introduced into delivery container 104 with a slower rate of injection so as to prevent the formation of a saturated layer of powder that could effectively act as a dam and seal dry areas of powder from the liquid 60. For smaller particles, exemplary results are experienced with a slow rate of liquid injection.

The description of the invention is merely exemplary in nature and, thus, variations that do not depart from the gist of the invention are intended to be within the scope of the invention. Such variations are not to be regarded as a departure from the spirit and scope of the invention.

What is claimed is:
1. A particulate packaging apparatus comprising:
a first container defining a first opening and a second opening;
a first sealing device removably coupled to the first container to seal the first opening;

a second sealing device removably coupled to the first container to seal the second opening, wherein the first container and the first and second sealing devices define a chamber;

an allograft contained within the chamber, the first container maintaining a negative pressure within the chamber; and a second container enclosing the first container and maintaining a negative pressure therein, wherein the first sealing device includes a valve for coupling to a source in order to draw the negative pressure on the chamber.

2. The apparatus of claim 1, wherein the first container is a syringe barrel.

3. The apparatus of claim 1, wherein the first sealing device is a vented valve.

4. The apparatus of claim 1, wherein the first sealing device is interconnected to the first container with a leur filling.

5. The apparatus of claim 1, wherein the second sealing device is adapted to slidingly translate within said chamber.

6. The apparatus of claim 5, further comprising a plunger at least partially inserted into the second opening and adapted to slidingly translate the second sealing device.

7. The apparatus of claim 1, wherein the first container is adapted for direct application of the allograft to a surgical site.

8. The apparatus of claim 1, wherein the second container is a vacuum bag.

9. The apparatus of claim 1, further comprising a third container adapted to removably couple to the second sealing device, wherein the third container is further adapted to deliver a liquid to the first container.

10. The apparatus of claim 9, wherein the third container is a syringe adapted to couple to the first container with a leur filling.

11. A particulate packaging apparatus comprising:
a first syringe defining a chamber including an opening for receipt of an allograft material;
a valve releasably coupled to the opening of the chamber of the first syringe, the valve including a first filling adapted to be coupled to a vacuum source to draw a negative pressure within the first syringe;
a second syringe defining a chamber including an opening for receipt of a reconstituting material; and
a second fitting coupled to the opening of the chamber of the second syringe,
wherein the second filling is coupled to the first filling of the valve in a delivery position.

12. The particulate packaging apparatus of claim 11 further comprising:
a container for releasably enclosing the first syringe and the second syringe to maintain the negative pressure within the first syringe,
wherein the container is adapted to be coupled to the vacuum source to draw a negative pressure within the container.

13. A particulate packaging apparatus comprising:
a first container defining a chamber including an opening;
a first sealing device removably coupled to the chamber of the first container to seal the opening, the first sealing device including a valve for coupling to a source in order to draw a negative pressure on the chamber of the first container;
an allograft contained within the chamber;
a second container defining a chamber for receipt of a reconstituting agent;
a second sealing device removably coupled to the chamber of the second container; and
a third container defining a cavity that maintains a negative pressure, the cavity housing the first container and the second container.

14. The particulate packaging apparatus of claim 13, wherein the first sealing device further includes a leur fitting.

15. The particulate packaging apparatus of claim 14, wherein the second sealing device further includes a leur fitting to selectively couple the second container to the first container through the first sealing device and the second sealing device.

16. The particulate packaging apparatus of claim 13, wherein the first container and the second container are syringes.

* * * * *

UNITED STATES PATENT AND TRADEMARK OFFICE
CERTIFICATE OF CORRECTION

PATENT NO. : 7,172,071 B2
APPLICATION NO. : 10/634468
DATED : February 6, 2007
INVENTOR(S) : H. G. Hawkins It is certified that error appears in the above-identified patent and that said Letters Patent is hereby corrected as shown below:

Column 3:
Line 26, delete "or second container".

Column 4:
Line 45, "FIGS." should be --FIG.--.

Column 7:
Line 19, claim 4, "filling" should be --fitting--.
Line 41, claim 11, "filling" should be --fitting--.

Column 8:
Line 5, claim 11, "filling" should be --fitting-- (both occurrences).

Signed and Sealed this

Thirty-first Day of March, 2009

JOHN DOLL
*Acting Director of the United States Patent and Trademark Office*